US012351186B2

United States Patent
Fuchs et al.

(10) Patent No.: US 12,351,186 B2
(45) Date of Patent: Jul. 8, 2025

(54) METHOD AND DEVICE FOR DETERMINING THE VITAL FUNCTIONS OF A VEHICLE OCCUPANT

(71) Applicant: Robert Bosch GmbH, Stuttgart (DE)

(72) Inventors: Tino Fuchs, Tuebingen (DE); Hans-Joachim Bieg, Weil Im Schoenbuch (DE); Robert Roelver, Calw-Stammheim (DE)

(73) Assignee: Robert Bosch GmbH, Stuttgart (DE)

( * ) Notice: Subject to any disclaimer, the term of this patent is extended or adjusted under 35 U.S.C. 154(b) by 0 days.

(21) Appl. No.: 18/571,682

(22) PCT Filed: Sep. 1, 2022

(86) PCT No.: PCT/EP2022/074353
§ 371 (c)(1),
(2) Date: Dec. 18, 2023

(87) PCT Pub. No.: WO2023/031339
PCT Pub. Date: Mar. 9, 2023

(65) Prior Publication Data
US 2024/0278789 A1 Aug. 22, 2024

(30) Foreign Application Priority Data
Sep. 6, 2021 (DE) ...................... 10 2021 209 759.6

(51) Int. Cl.
*B60W 40/08* (2012.01)
*B60W 50/00* (2006.01)

(52) U.S. Cl.
CPC ........ *B60W 40/08* (2013.01); *B60W 50/0098* (2013.01); *B60W 2040/0818* (2013.01);
(Continued)

(58) Field of Classification Search
None
See application file for complete search history.

(56) References Cited

U.S. PATENT DOCUMENTS 8,706,204 B2   4/2014   Seo et al.
10,210,409 B1  2/2019   Migneco et al.
(Continued)

OTHER PUBLICATIONS

International Search Report corresponding to PCT Application No. PCT/EP2022/074353, mailed Jan. 2, 2023 (German and English language document) (5 pages).
(Continued)

*Primary Examiner* — Thomas S McCormack
(74) *Attorney, Agent, or Firm* — Maginot, Moore & Beck LLP

(57) ABSTRACT

A method for determining the vital functions of a vehicle occupant enables precise measurements and is easy to use without negatively affecting the vehicle occupant. The method includes determining the vital functions of the vehicle occupant using a sensor device integrated in a vehicle seat of a motor vehicle, and acquiring measurement signals of the vehicle occupant from which cardiogram signals are acquired. The method further includes using an evaluation unit to ascertain the vital functions of the vehicle occupant from the cardiogram signals. The sensor device is a magnetic field sensor device, and the cardiogram signals are magnetic cardiogram signals.

20 Claims, 3 Drawing Sheets

(52) U.S. Cl.
CPC . *B60W 2050/0054* (2013.01); *B60W 2420/50* (2013.01); *B60W 2540/22* (2013.01); *B60W 2540/221* (2020.02)

(56) References Cited

U.S. PATENT DOCUMENTS

| | | | | |
|---|---|---|---|---|
| 2009/0326399 | A1* | 12/2009 | Barrero Batalloso ... | A61B 5/18 600/509 |
| 2014/0039330 | A1* | 2/2014 | Seo .................... | A61B 5/02255 600/509 |
| 2021/0103010 | A1* | 4/2021 | Rosenfeld ............. | G01R 33/24 |

OTHER PUBLICATIONS

Arai et al., "Millimetre-scale magnetocardiography of living rats using a solid-state quantum sensor," arxiv.org, Cornell University Library, 201 Olin Library Cornell University, May 25, 2021 (17 pages).

* cited by examiner

METHOD AND DEVICE FOR DETERMINING THE VITAL FUNCTIONS OF A VEHICLE OCCUPANT

This application is a 35 U.S.C. § 371 National Stage Application of PCT/EP2022/074353, filed on Sep. 1, 2022, which claims the benefit of priority to Serial No. DE 10 2021 209 759.6, filed on Sep. 6, 2021 in Germany, the disclosures of which are incorporated herein by reference in their entirety.

The disclosure relates to a method and a device for determining the vital functions of a vehicle occupant, wherein cardiogram signals of a vehicle occupant are acquired without contact by a sensor device integrated into a vehicle seat of a motor vehicle, wherein the cardiogram signals are transmitted to an evaluation unit, wherein the evaluation unit ascertains vital functions of the vehicle occupant from the cardiogram signals.

The disclosure also relates to a motor vehicle comprising a vehicle seat and an evaluation unit.

BACKGROUND

In the field of developing mobility solutions, autonomous driving, health, and passenger safety are becoming increasingly important.

Identifying the behavior of a driver and the other vehicle occupants has already become an integral part of motor vehicles. Seat occupancy detection in combination with the seat belt sensor or driver fatigue detection, for instance, are well-known.

Efforts are also being made to acquire a wider range of vital parameters for a driver. This makes it possible to determine the fitness or health of the driver. Health-related information can be used by driver assistance systems to initiate an emergency stop of the motor vehicle in the event of an emergency. This protects not only the driver and other occupants, but also uninvolved potential accident victims and prevents serious accidents.

Capacitive methods for measuring cardiac activity, which can read seat occupancy via a change in capacitance of the seat heating electronics and a movement of the chest caused by the heartbeat, are known from the prior art. However, these methods are very inaccurate. Other known, but likewise inaccurate, methods use camera-, UWB-, or radar-based measurements.

Detecting a medical emergency, for example a heart attack, is currently possible only via a direct derivation of the heart muscle signals. This usually occurs via electrodes having direct skin contact and is therefore unsuitable for comfortable integration in a motor vehicle.

A system for observing the heart rate of a passenger is known from U.S. Pat. No. 8,706,204 B2. The system includes a plurality of different types of heart rate sensors which are disposed on a seat cushion or seat back. The heart rate sensors are configured as electrocardiogram sensors.

A system for contactless acquisition of an electrodermal potential integrated in a motor vehicle is known from U.S. Pat. No. 10,210,409 B1. The electrodermal potential can be used to ascertain an awake or sleeping state of a vehicle occupant.

SUMMARY

The underlying object of the disclosure is to provide a method for determining the vital functions of a vehicle occupant, which enables precise measurements and is easy to use without negatively affecting the vehicle occupant.

To achieve the underlying object of the disclosure, a method for determining the vital functions of a vehicle occupant is proposed, wherein measurement signals of a vehicle occupant are acquired without contact by means of a sensor device integrated into a vehicle seat of a motor vehicle, wherein cardiogram signals are acquired from the measurement signals, wherein an evaluation unit ascertains vital functions of the vehicle occupant from said cardiogram signals, wherein it is further provided that the sensor device is a magnetic field sensor device and that the cardiogram signals are magnetic cardiogram signals.

The evaluation unit can infer the state of the vehicle occupant's fitness and health from the magnetic cardiogram signals. The evaluation of the magnetic cardiogram signals in particular makes it possible to detect medically relevant cardiac emergencies early and initiate a safe vehicle stop before the vehicle occupant loses control of the vehicle and endangers themselves and others.

It is preferably provided that the magnetic field sensor device is a gradiometer comprising at least two magnetic field sensors disposed at spaced-apart positions, wherein the at least two magnetic field sensors measure a magnetic field at the spaced-apart positions and generate the measurement signals, wherein the magnetic cardiogram signal is further preferably ascertained as a difference signal of the measurement signals of the at least two magnetic field sensors.

The magnetic fields generated by the heart muscle have a strength in the range of 100 pT. These magnetic field strengths are well below typical magnetic field strengths in the environment. The Earth's magnetic field strength is approximately 50 μT and the magnetic fields in the motor vehicle range from 1 to 10 nT. By configuring the magnetic field sensor device as a gradiometer comprising two magnetic field sensors disposed at spaced-apart positions, these interference fields from the environment can be eliminated. For this purpose, the magnetic field is measured simultaneously with two magnetic field sensors. The interference fields from the environment, which have the same field strength at the two positions of the magnetic field sensors, can be eliminated by calculating the difference between the measurement signals from the at least two magnetic field sensors. Only the magnetic field generated by the heart remains in the difference signal in the form of the magnetic cardiogram signal, because the magnetic field generated by the heart has a high gradient between the two positions of the magnetic field sensors.

The difference signal can be generated directly by the magnetic field sensor device. However, it is also possible that the difference signal is generated in the evaluation unit, in which case the measurement signals of the magnetic field sensors are transmitted to the evaluation unit.

It is preferably provided that the at least two magnetic field sensors have a distance to one another of 0.5 cm to 2 cm, further preferably 1 cm to 1.5 cm.

The applicant's investigations have shown that measurement of the biomagnetic fields, for example the magnetic fields generated by a heart, is ideal when the distance is between 0.5 cm to 2 cm.

With further advantage, it can be provided that a plurality of the magnetic field sensor devices are provided and/or that the magnetic field sensor device in the vehicle seat is automatically positioned in proximity to the heart of the vehicle occupant.

Since there can be a very large spread or variance in the size of possible vehicle occupants, it is advantageous if multiple magnetic field sensor devices are integrated in the vehicle seat at different positions. Alternatively or additionally, it can be provided that the magnetic field sensor device is actively positioned in the vehicle seat, so that the magnetic field sensor device is always positioned in close proximity to the heart, regardless of the size of the vehicle occupant. This can ensure that a sufficiently strong magnetic cardiogram signal can be acquired.

Further preferably, it is provided that the magnetic field sensor device is disposed in a backrest of the vehicle seat.

It is preferably provided that the magnetic field sensors are nitrogen vacancy sensors, wherein each nitrogen vacancy sensor preferably comprises a diamond, optical filters, and photodetectors, and further preferably a microwave resonator and/or a light source, in particular a laser.

However, the microwave resonator and/or the light source can also be disposed spaced apart from the magnetic field sensor device or by the magnetic field sensors.

It is in principle possible to use TMR, GMR or Hall sensors, SQUID sensors or vapor cell magnetometers to measure the magnetic fields to ascertain the magnetic cardiogram signals. However, such sensors generally do not have sufficiently high sensitivity. Although highly sensitive, superconducting SQUID sensors have sufficient accuracy, they require active cooling with liquid nitrogen or helium and are therefore less suitable for use in a vehicle seat. Although vapor cell magnetometers have the necessary sensitivity, they have only a limited dynamic range.

It is therefore preferably provided that the magnetic field sensors are nitrogen vacancy sensors. Nitrogen vacancy sensors are based on measuring a fluorescence spectrum of nitrogen centers in a diamond. The spectrum of a diamond with nitrogen vacancies shows fluorescence in the red wavelength range when it is optically excited. If microwave radiation is radiated in in addition to the optical excitation, there is a drop in the fluorescence at 2.88 GHz because, in this case, the electrons are raised from the $m_s=0$ level of the 3A state to the $m_s=+/-1$ level of the 3E state, from which they recombine in a non-radiative manner. In the presence of an external magnetic field, splitting of the $m_s$ level occurs, also known as Zeeman splitting, and, when the fluorescence is plotted over the frequency of the microwave excitation, two dips appear in the fluorescence spectrum, the frequency spacing of which is proportional to the magnetic field strength. The magnetic field sensitivity is defined by the minimally resolvable frequency shift and can reach 1 pT. Because the nitrogen vacancy center in the single-crystal diamond has four possible ways to position itself in the crystal lattice, the presence of a directed magnetic field causes the nitrogen vacancy centers present in the crystal to react differently to the external magnetic field depending on their position in the crystal. In the maximum case, therefore, four pairs of fluorescence minima associated with one another can appear in the spectrum, from the shape and position relative to one another of which the amount and direction of the magnetic field can be clearly determined.

The design and mode of operation of a nitrogen vacancy sensor are moreover known to those skilled in the art.

With further advantage, it can be provided that the magnetic cardiogram signals are filtered by the evaluation unit with a high-pass filter and/or a low-pass filter, and/or that the evaluation unit ascertains a bias drift of the magnetic field sensors, in particular by averaging the magnetic cardiogram signals over a period of time that is greater than the heart rate.

Filtering with a low-pass filter eliminates noise components having frequencies well above the heart rate. It is also possible to subtract the bias drift from the high-pass and/or low-pass filtered signal to obtain a clean magnetic cardiogram signal.

It is further preferably provided that the evaluation unit ascertains vital parameters from the magnetic cardiogram signals; preferably a heart rate, and/or a heart rate variability, and/or a duration and/or amplitude of ECG-equivalent signal changes, preferably P wave, QRS complex, T wave, and corresponding combinations.

With further advantage, it can be provided that the evaluation unit determines the vital functions of the vehicle occupant based on the vital parameters, wherein the evaluation unit preferably creates an assessment of whether the vehicle occupant is tired or awake, stressed or relaxed, whether an acute or chronic abnormality in cardiac function is present or imminent, or whether there are underlying diseases that impair cardiac function.

A variety of methods can be used to determine the vital functions of the vehicle occupant based on the vital parameters. It is possible to use a threshold value method based on a given table with relevant normal values, wherein the normal values can be taken from clinical diagnostics. A data-driven evaluation or interpretation with the aid of a statistical classification method is possible as well. A decision tree method or a random forest method can be used here. Another option is to employ an evaluation that uses deep neural networks.

It is preferably provided that further measures are taken based on the assessment, wherein the further measures include an emergency stop of the motor vehicle and/or placing an emergency call and/or transmitting the vital functions to medical personnel.

Additionally or alternatively, the driver can actively be warned that a medical issue has been identified. If the evaluation unit places an emergency call, the vital functions, vital parameters, magnetic cardiogram signals, or the assessment can be sent to the medical personnel at the same time along with the emergency call, thereby enabling optimal treatment of the vehicle occupant without further delay of an on-site ECG measurement.

Other information, such as the age or weight of the vehicle occupant, can also be included when creating the assessment. The other information can be included via interfaces, such as a multimedia or infotainment system or an app.

It can also preferably be provided that the evaluation unit sends the vital functions and/or the assessment to other motor vehicle systems, in particular to an infotainment system, a driver assistance system, or a comfort system.

If the vital function and/or the assessment are passed to a comfort system, for instance, a massage function, scenting of the vehicle interior, or ambient lighting can be activated. The vital functions and the assessment can moreover contribute to improving fatigue detection and thus improve the accuracy of a rest recommendation. For this purpose, the method can be combined with the evaluation of data from an interior camera.

The assessment can be provided with a confidence value that reflects the statistical certainty of the classification result or the assessment.

Advantageous is a device configured for determining the vital functions of a vehicle occupant as described above and comprising a sensor device, which is designed to be installed in a vehicle seat of a vehicle, in particular a motor vehicle, and is configured to acquire measurement signals of a vehicle occupant, wherein the sensor device is embodied as a magnetic field sensor device, and further comprising an evaluation unit, which is communicatively connected to the magnetic field sensor device and is configured to ascertain the vital functions of a vehicle occupant from the cardiogram signals obtained from the measurement signals, wherein the cardiogram signals are magnetic cardiogram signals.

In an advantageous configuration, it can be provided that the sensor device or also the sensor device and the evaluation unit are disposed in the vehicle seat.

It is readily apparent that it can be advantageous to integrate the sensor device or the sensor device evaluation device into the vehicle seat as part of the production of said vehicle seat.

The evaluation device can advantageously be implemented in the form of a software module in a control unit or computer. It is therefore also possible to integrate the evaluation device into an already existing control unit or a computer in the vehicle, for example an infotainment computer or a central computer, which can be connected to the sensor device via discrete lines, a wired data bus, or via a radio interface. A further solution of the underlying object of the disclosure is to provide a motor vehicle comprising a vehicle seat and an evaluation unit configured to carry out a previously described method.

All functions, features, and configurations discussed in connection with the previously described method can be applied in the same way to the motor vehicle as well.

BRIEF DESCRIPTION OF THE DRAWINGS

The disclosure is explained in more detail in the following with reference to the accompanying figures.

The figures show.

DETAILED DESCRIPTION

A method 100 for determining the vital functions of a vehicle occupant 10 is explained in more detail in the following with reference to the figures.

Figure 1:
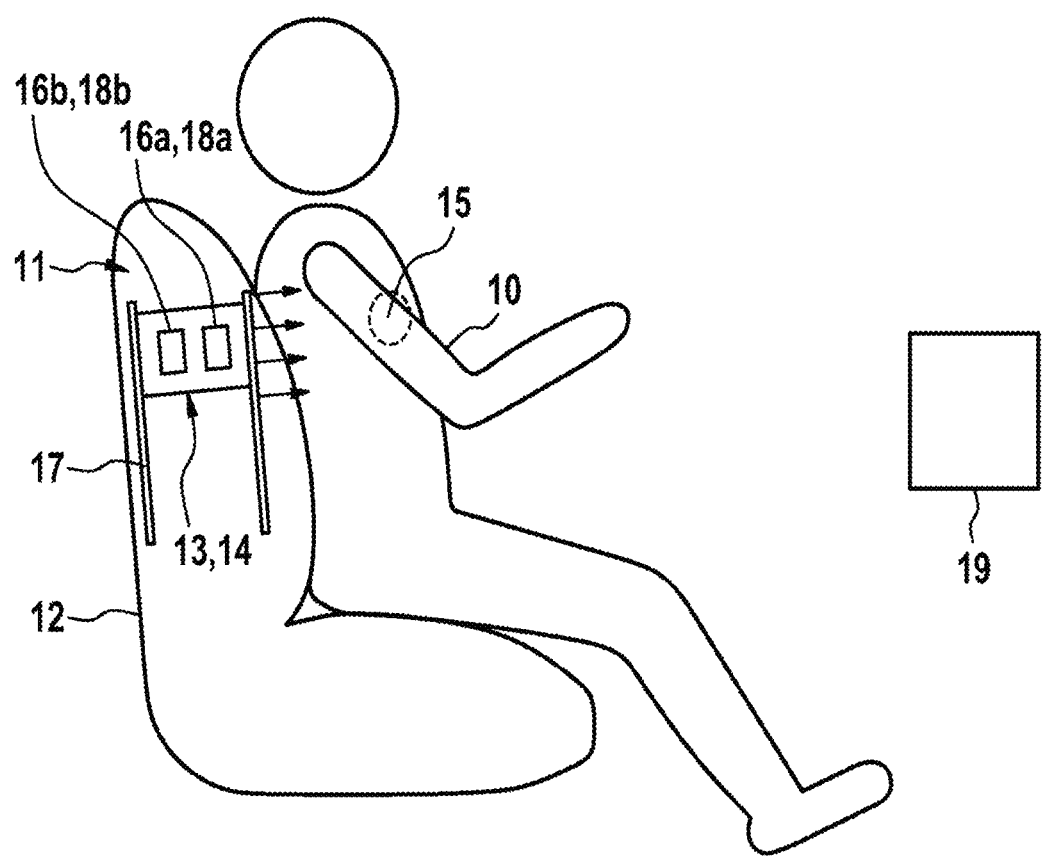
FIG. 1 a vehicle seat comprising a magnetic field sensor device.
Figure 3:
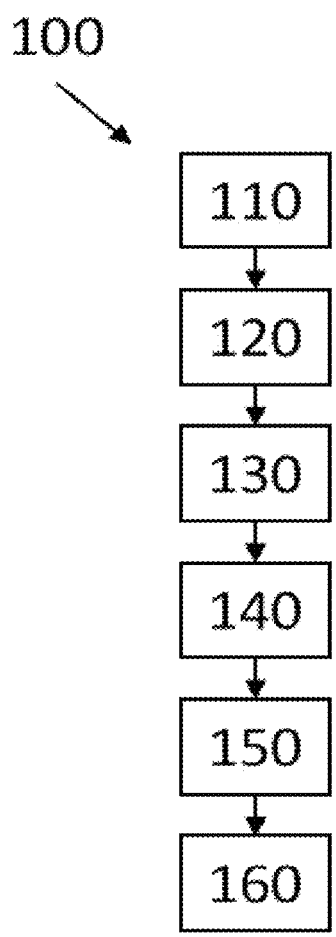
FIG. 3 a flowchart of the method.

According to the method, a vehicle seat 11 of a not further depicted motor vehicle is provided and is shown in FIG. 1. A sensor device 13 is disposed in the vehicle seat 11, in particular in the backrest 12. The sensor device 13 is configured as a magnetic field sensor device 14 and acquires measurement signals of a heart 15 of the vehicle occupant 10 (FIG. 3, Step 110). The magnetic field sensor device 14 comprises two magnetic field sensors 16*a*, 16*b* which are disposed at spaced-apart positions. A first magnetic field sensor 16*a* is disposed closer to the heart 15 of the vehicle occupant 10 than a second magnetic field sensor 16*b*. The two magnetic field sensors 16*a*, 16*b* thus measure the magnetic field at the spaced-apart positions and respectively generate the measurement signals. The measurement signals acquired by the magnetic field sensors 16*a*, 16*b* are transmitted to an evaluation unit 19 by radio or wire (FIG. 3, Step 120). By calculating the difference between the measurement signals of the two magnetic field sensors 16*a*, 16*b*, interference fields, such as the Earth's natural magnetic field or magnetic fields occurring in the motor vehicle, can be eliminated. The difference signal of the measurement signals is a magnetic cardiogram signal. The evaluation unit 19 ascertains vital parameters from the magnetic cardiogram signals (FIG. 3, Step 130). For this purpose, the magnetic cardiogram signals are first filtered with a low-pass filter. A bias drift of the magnetic field sensors 16*a*, 16*b* is then ascertained by averaging the magnetic cardiogram signals over a period of time that is greater than the heart rate. The bias drift of the magnetic field sensors 16*a*, 16*b* is subtracted from the magnetic cardiogram signals. From the vital parameters, which can be a heart rate and/or a heart rate variability for instance, the evaluation unit 19 ascertains the vital functions of the vehicle occupant 10 and creates an assessment of a current state or a mental or physical condition of the vehicle occupant (Step 140). This state can, for instance, include an assessment of whether the vehicle occupant 10 is tired or awake, stressed or relaxed, whether an acute or chronic abnormality in cardiac function is present or imminent, or whether there are underlying diseases that impair cardiac function. If the evaluation unit 19 determines that there is a vital function that impairs the driving ability of the vehicle occupant 10, the evaluation unit 19 sends the vital functions and/or the assessment to other motor vehicle systems, such as a driver assistance system (Step 150). The driver assistance system is preferably configured to carry out further measures depending on the information received from the evaluation unit about the condition of the vehicle occupant, for example placing an automatic emergency call (e-call) to a control center, bringing the vehicle to a controlled stop, or initiating other helpful or meaningful measures based on the state of the vehicle occupant (Step 160). The two magnetic field sensors 16*a*, 16*b* have a distance of 0.5 cm to 2 cm from one another. The magnetic field sensor device 14 is configured as a gradiometer and is height adjustable by means of a guide system 17 in the backrest 12, so that the magnetic field sensor device 14 can always be positioned in proximity to the heart 15 of the vehicle occupant 10. The two magnetic field sensors 16*a*, 16*b* are configured as nitrogen vacancy sensors 18*a*, 18*b* and comprise a diamond, optical filters, and photodetectors that are not shown in detail.

Figure 2:
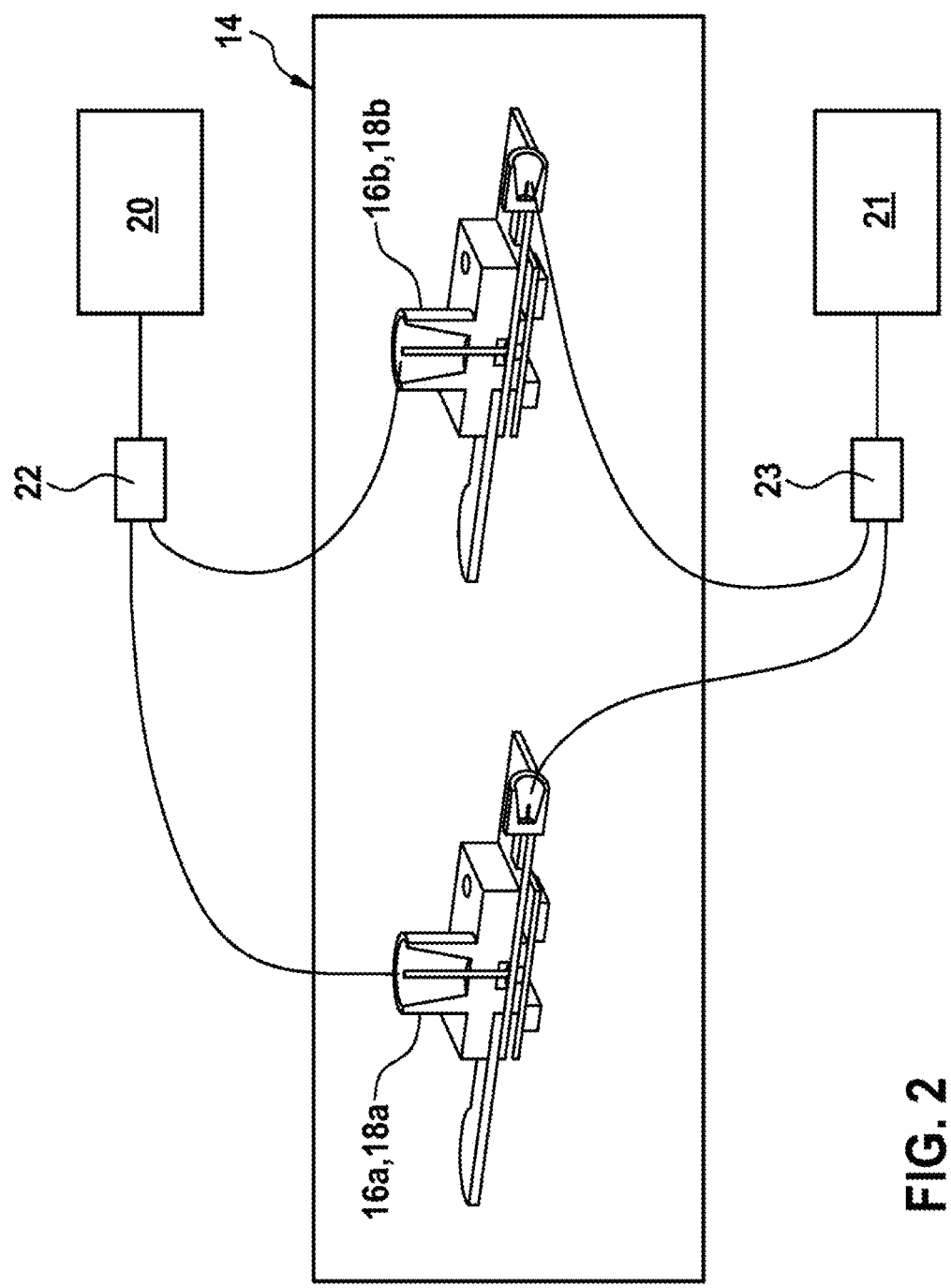
FIG. 2 a magnetic field sensor device.

FIG. 2 shows a detail view of the magnetic field sensor device 14 of FIG. 1. The magnetic field sensor device 14 comprises two magnetic field sensors 16*a*, 16*b* which are configured as nitrogen vacancy sensors 18*a*, 18*b*. The two magnetic field sensors 16*a*, 16*b* are disposed at a distance of 0.5 cm to 2 cm from one another and each comprise a nitrogen vacancy doped diamond, optical filters, and photodetectors. The magnetic field sensor device 14 further comprises a laser 20 and a microwave resonator 21. The two nitrogen vacancy sensors 18*a*, 18*b* are exposed to light by the laser 20 and a fiber splitter 22 is provided in the beam path. The microwave resonator 21 furthermore radiates microwave radiation onto the nitrogen vacancy sensors 18*a*, 18*b*, wherein a microwave splitter 23 is disposed in the beam path.

The invention claimed is:

1. A method for determining vital functions of a vehicle occupant, comprising:

acquiring measurement signals of the vehicle occupant using a sensor device integrated in a vehicle seat of a motor vehicle;

acquiring cardiogram signals from the measurement signals; and ascertaining the vital functions of the vehicle occupant from the cardiogram signals using an evaluation unit, wherein the sensor device is a magnetic field sensor device, wherein the cardiogram signals are magnetic cardiogram signals, wherein the evaluation unit ascertains vital parameters from the magnetic cardiogram signals including a heart rate, a heart rate variability, and/or a duration and/or amplitude of ECG-equivalent signal changes including P wave, QRS complex, T wave, and corresponding combinations,
wherein the evaluation unit determines the vital functions of the vehicle occupant based on the vital parameters using a statistical classification method, and
wherein the evaluation unit creates an assessment of whether the vehicle occupant is tired or awake, stressed or relaxed, whether an acute or chronic abnormality in cardiac function is present or imminent, and/or whether there are underlying diseases that impair cardiac function of the vehicle occupant.

2. The method according to claim 1, wherein:
the magnetic field sensor device is a gradiometer comprising at least two magnetic field sensors disposed at spaced-apart positions,
the at least two magnetic field sensors measure a magnetic field at the spaced-apart positions and generate the measurement signals, and
the cardiogram signals are ascertained as a difference signal of the measurement signals of the at least two magnetic field sensors.

3. The method according to claim 2, wherein:
the at least two magnetic field sensors are nitrogen vacancy sensors, and
each of the nitrogen vacancy sensors comprises a diamond, optical filters, photodetectors, and a microwave resonator and/or a laser.

4. The method according to claim 1, wherein:
further measures are taken based on the assessment, and
the further measures include an emergency stop of the motor vehicle, placing an emergency call, and/or transmitting the vital functions to medical personnel.

5. The method according to claim 1, wherein:
the evaluation unit sends the vital functions and/or the assessment to other motor vehicle systems including an infotainment system, a driver assistance system, and/or a comfort system.

6. A method for determining vital functions of a vehicle occupant, comprising:
acquiring measurement signals of the vehicle occupant using a sensor device integrated in a vehicle seat of a motor vehicle;
acquiring cardiogram signals from the measurement signals; and
ascertaining the vital functions of the vehicle occupant from the cardiogram signals using an evaluation unit,
wherein the sensor device is a magnetic field sensor device,
wherein the cardiogram signals are magnetic cardiogram signals,
wherein the magnetic field sensor device is a gradiometer comprising at least two magnetic field sensors disposed at spaced-apart positions,
wherein the at least two magnetic field sensors measure a magnetic field at the spaced-apart positions and generate the measurement signals,
wherein the cardiogram signals are ascertained as a difference signal of the measurement signals of the at least two magnetic field sensors, and
wherein the magnetic cardiogram signals are filtered by the evaluation unit with a high-pass filter and/or a low-pass filter, and/or the evaluation unit ascertains a bias drift of the at least two magnetic field sensors by averaging the magnetic cardiogram signals over a period of time that is greater than a heart rate of the vehicle occupant.

7. The method according to claim 6, wherein a plurality of the magnetic field sensor devices are provided.

8. The method according to claim 6, wherein the evaluation unit ascertains vital parameters from the magnetic cardiogram signals including a heart rate, a heart rate variability, and/or a duration and/or amplitude of ECG-equivalent signal changes including P wave, QRS complex, T wave, and corresponding combinations.

9. The method according to claim 6, wherein:
the at least two magnetic field sensors are nitrogen vacancy sensors, and
each of the nitrogen vacancy sensors comprises a diamond, optical filters, photodetectors, and a microwave resonator and/or a laser.

10. The method according to claim 6, wherein the magnetic field sensor device is automatically positioned in proximity to a heart of the vehicle occupant.

11. The method according to claim 6, wherein:
the evaluation unit ascertains vital parameters from the magnetic cardiogram signals including a heart rate, a heart rate variability, and/or a duration and/or amplitude of ECG-equivalent signal changes including P wave, QRS complex, T wave, and corresponding combinations,
the evaluation unit determines the vital functions of the vehicle occupant based on the vital parameters using a statistical classification method, and
the evaluation unit creates an assessment of whether the vehicle occupant is tired or awake, stressed or relaxed, whether an acute or chronic abnormality in cardiac function is present or imminent, and/or whether there are underlying diseases that impair cardiac function of the vehicle occupant.

12. The method according to claim 11, wherein:
further measures are taken based on the assessment, and
the further measures include an emergency stop of the motor vehicle, placing an emergency call, and/or transmitting the vital functions to medical personnel.

13. The method according to claim 11, wherein:
the evaluation unit sends the vital functions and/or the assessment to other motor vehicle systems including an infotainment system, a driver assistance system, and/or a comfort system.

14. A device for determining vital functions of a vehicle occupant, comprising:
a sensor device installed in a vehicle seat of a motor vehicle, and configured to ascertain measurement signals of a vehicle occupant, the sensor device embodied as a magnetic field sensor device; and
an evaluation unit configured to ascertain the vital functions of the vehicle occupant from cardiogram signals obtained from the measurement signals,
wherein the cardiogram signals are magnetic cardiogram signals,
wherein the magnetic field sensor device is a gradiometer comprising at least two magnetic field sensors disposed at spaced-apart positions,
wherein the at least two magnetic field sensors measure a magnetic field at the spaced-apart positions and generate the measurement signals,
wherein the cardiogram signals are ascertained as a difference signal of the measurement signals of the at least two magnetic field sensors, and wherein the magnetic cardiogram signals are filtered by the evaluation unit with a high-pass filter and/or a low-pass filter, and/or the evaluation unit ascertains a bias drift of the at least two magnetic field sensors by averaging the magnetic cardiogram signals over a period of time that is greater than a heart rate of the vehicle occupant.

15. The device according to claim 14, wherein the evaluation unit is disposed in the vehicle seat.

16. The device according to claim 14, wherein:
the magnetic field sensor device is a gradiometer comprising at least two magnetic field sensors disposed at spaced-apart positions,
the at least two magnetic field sensors measure a magnetic field at the spaced-apart positions and generate the measurement signals, and
the cardiogram signals are ascertained as a difference signal of the measurement signals of the at least two magnetic field sensors.

17. The device according to claim 14, wherein the magnetic field sensor device is automatically positioned in proximity to a heart of the vehicle occupant.

18. The device according to claim 14, wherein:
the evaluation unit ascertains vital parameters from the magnetic cardiogram signals including a heart rate, a heart rate variability, and/or a duration and/or amplitude of ECG-equivalent signal changes including P wave, QRS complex, T wave, and corresponding combinations,
the evaluation unit determines the vital functions of the vehicle occupant based on the vital parameters using a statistical classification method, and
the evaluation unit creates an assessment of whether the vehicle occupant is tired or awake, stressed or relaxed, whether an acute or chronic abnormality in cardiac function is present or imminent, and/or whether there are underlying diseases that impair cardiac function of the vehicle occupant.

19. The device according to claim 18, wherein:
further measures are taken based on the assessment, and
the further measures include an emergency stop of the motor vehicle, placing an emergency call, and/or transmitting the vital functions to medical personnel.

20. The device according to claim 18, wherein:
the evaluation unit sends the vital functions and/or the assessment to other motor vehicle systems including an infotainment system, a driver assistance system, and/or a comfort system.

* * * * *